United States Patent [19]
Frey et al.

[11] Patent Number: 5,998,024
[45] Date of Patent: *Dec. 7, 1999

[54] BIOCOMPATIBLE MATERIAL AND METHOD OF MANUFACTURE AND USE THEREOF

[75] Inventors: Rainer H. Frey, Watzmannstrasse 10, D-82319 Starnberg; Lothar Sellin, Keltenstrasse 35, D-52074 Aachen, both of Germany

[73] Assignees: Rainer H. Frey, Starnberg; Lothar Sellin, Aachen; H. Peter Brehm, Starnberg, all of Germany

[ * ] Notice: This patent is subject to a terminal disclaimer.

[21] Appl. No.: 08/533,963

[22] Filed: Sep. 26, 1995

[30] Foreign Application Priority Data

| | | | |
|---|---|---|---|
| Feb. 2, 1995 | [DE] | Germany | 195 03 391 |
| May 15, 1995 | [DE] | Germany | 195 17 727 |

[51] Int. Cl.$^6$ ................. B05D 5/00; D02G 3/00
[52] U.S. Cl. ............ 428/367; 428/364; 428/375; 428/394; 428/408; 428/378; 427/244; 427/412.3
[58] Field of Search .................. 428/364, 375, 428/408, 367, 378, 400, 394; 427/244, 412.3

[56] References Cited

U.S. PATENT DOCUMENTS

| | | | |
|---|---|---|---|
| 3,276,448 | 10/1966 | Kronenthal et al. | 128/334 |
| 3,526,005 | 9/1970 | Bokros et al. | 3/1 |
| 3,685,059 | 8/1972 | Bokros et al. | 3/1 |
| 3,809,669 | 5/1974 | Rainer | 260/2.5 R |
| 3,952,334 | 4/1976 | Bokros et al. | 3/1 |
| 4,164,045 | 8/1979 | Bokros et al. | 3/1.4 |
| 4,457,984 | 7/1984 | Otani et al. | 428/220 |
| 4,690,763 | 9/1987 | Rieger et al. | 210/496 |
| 4,699,681 | 10/1987 | Kasmark, Jr. et al. | 156/264 |
| 4,718,907 | 1/1988 | Karwoski et al. | 623/12 |
| 4,808,315 | 2/1989 | Manabe et al. | 210/645 |
| 4,816,332 | 3/1989 | Fujita et al. | 428/304 |
| 5,104,425 | 4/1992 | Rao et al. | 55/16 |
| 5,124,177 | 6/1992 | Kasmark, Jr. et al. | 427/202 |
| 5,171,492 | 12/1992 | Kawakubo | 264/296 |
| 5,286,424 | 2/1994 | Su et al. | 264/23 |
| 5,336,164 | 8/1994 | Snider et al. | 604/4 |
| 5,370,684 | 12/1994 | Vallana et al. | 623/1 |
| 5,435,836 | 7/1995 | Anand et al. | 95/45 |
| 5,543,218 | 8/1996 | Bennett et al. | 428/375 |
| 5,681,657 | 10/1997 | Frey et al. | 428/375 |

FOREIGN PATENT DOCUMENTS

| | | |
|---|---|---|
| 0 002 090 A1 | 5/1979 | European Pat. Off. ........ A61L 17/00 |
| 0 302 717 A1 | 2/1989 | European Pat. Off. .......... A61F 2/30 |
| 0 575 945 A2 | 12/1993 | European Pat. Off. ........ B01D 53/22 |
| 30 13 357 A1 | 10/1981 | Germany ...................... B01D 13/04 |
| 1111708 | 4/1989 | Japan . |
| 801531 | 9/1958 | United Kingdom . |
| 856329 | 12/1960 | United Kingdom . |
| 1 226 833 | of 1971 | United Kingdom . |

OTHER PUBLICATIONS

Howell, B.A., Warner, B.S., Rajaram, C.V., Ahmed, S.I., and Ahmed, Z., "Stabilization of Vinylidene Chloride Barrier Resins", *Polymers for Advanced Technologies*, vol. 5, pp. 485–492, Sep. 1994.

Snimshchikova, A.A., Vlasov, A.V., L'vov, V.A., and Tsetlin, B.L., "Kinetic Characteristics of Radiation Graft Polymerization of Vinylidene Chloride from the Gas Phase Onto Polypropylene Fibre", *Polymer Science USSR*, vol. 29, No. 10, pp. 2335–2338, 1987.

Rao, M.B. and Sircar, S., "Nanoporous Carbon Membranes for Separation of Gas Mixtures by Selective Surface Flow", *Journal of Membrane Science*, vol. 85, No. 2, Dec. 2, 1993, pp. 253–264.

CA Abstract No. 08781 D/06 TOYJ 24.0.5.79.
CA Abstract No. 69927 A/39 HITM 04.02.77.
Müller et al., German Language Survey Article (1986), vol. 57, pp. 64–71 concerning Vascular Prostheses.

*Primary Examiner*—William Krynski
*Assistant Examiner*—J. M. Gray
*Attorney, Agent, or Firm*—Pollock, Vande Sande & Amernick

[57] ABSTRACT

A biocompatible material comprising a substrate made of a polyolefin material, and having a coating of biocompatible carbon material, wherein the coating is obtained by a process comprising the following steps:

- introducing a preformed substrate into an atmosphere of gaseous monomer vinylidene chloride (1,1 di-chloro ethylene);
- inducing a graft-polymerization reaction and grafting a uniform layer of polyvinylidene chloride on the substrate; and
- substantially eliminating and removing hydrogen chloride (dehydrochlorination reaction) from the polyvinylidene chloride in order to convert the polyvinylidene chloride layer into a coating of biocompatible carbon material.

25 Claims, No Drawings

BIOCOMPATIBLE MATERIAL AND METHOD OF MANUFACTURE AND USE THEREOF

TECHNICAL FIELD

The present invention relates to a biocompatible material comprising a substrate made of a polyolefin material and having a coating of a biocompatible carbon material. In the present context "biocompatible" means especially excellent compatibility with respect to blood and tissue; in particular, biocompatibility includes haemocompatibility and thromboresistance. The biocompatible material according to the present invention is especially suited for the manufacture of medical prosthetic devices intended for prolonged or permanent implantation in a living body. Further, this biocompatible material according to the present invention may be used for providing surfaces which will contact blood and/or plasma in oxygenators, in dialyzer devices, and in other equipment for maintaining extracorporal circulation of blood and/or plasma.

Further, the present invention relates to a method of manufacturing the biocompatible material.

Moreover, the present invention relates to specific kinds of uses of the biocompatible material, especially for implantation purposes, for example as artificial vascular grafts and other prosthetic devices, as suture material, suture rings for artificial prosthetic heart valves, as covering materials and cushions, as artificial ligaments and tendons and for other purposes in the field of medical prosthetic devices.

BACKGROUND ART

Among the actually available biocompatible materials, pyrolytic carbon seems to be one of the materials having the best biocompatible characteristics. Typically, the pyrolysis of carbon containing starting materials and depositing the so formed pyrolytic carbon on a substrate requires high temperatures in the range of from 800 to 1000° C. and higher. Medical prosthetic devices for implantation of this kind and methods of manufacture are disclosed in U.S. Pat. Nos. 4,164,045, 3,952,334, 3,685,059 and 3,526,005. The common substrate materials, especially materials based on organic polymers, will be irreversibly impaired by such high temperatures. European Patent Specification EP 0 224 080 B1 and U.S. Pat. No. 5,370,684 disclose a method for manufacturing a prosthetic device, comprising a substrate made of an organic polymer ("DACRON", "TEFLON") and having a coating of biocompatible carbon material. The coating has been deposited on the substrate at relatively low temperatures by sputtering a carbon target at a given voltage and current. The thus obtained coating has a thickness of less than 1.0 micron. The thus obtained carbon material is said to consist of turbostratic carbon. The known method is complex and expensive and provides a relatively low productivity. In case of an improper contact, the extremely thin carbon layer may easily be stripped off from the substrate.

According to other proposals, for example British Patents 856,329 or 801,531, the characteristics of polymer substrates may be modified and/or improved by grafting a coating on the surface of the substrates. The grafted polymer layer may be obtained by means of radical graft polymerization starting from ethylenic unsaturated monomers. The radical graft polymerization reaction may be induced by ionizing radiation. A typical ethylenic unsaturated monomer is methyl acrylate. An extended list of other suited monomers includes vinylidene chloride. By means of the grafted coating, a number of different characteristics may be obtained or improved; however, the preparation of a coating comprising biocompatible characteristics is not stated.

Contrary thereof, there is still an existing demand for a relatively simple method for preparing in high productivity, a biocompatible material comprising a biocompatible carbon material which is chemically bound to a substrate.

SUMMARY OF INVENTION

Accordingly, it is an object of the present invention to provide a biocompatible material comprising a substrate made of polyolefin material and having a coating of biocompatible carbon material, wherein the carbon material is chemically bound to the substrate.

It is a further object of the present invention to provide a method of manufacturing the biocompatible material using relatively simple process steps and providing high productivity and a constant quality of the product. Especially, the method provides a coating of carbon material having excellent compatibility with respect to blood (haemocompatibility) and high thromboresistance.

It is another object of the present invention to provide medical prosthetic devices for implantation purposes such as artificial vascular grafts, suture material and flexible fabrics and cushions for reconstructive surgery made of coated fibers, filaments, threads and multifilament yarns, which have been coated with a biocompatible carbon material according to the present invention.

In general, the biocompatible material according to the present invention comprises a substrate made of a polyolefin material and having a coating of a biocompatible carbon material, wherein the biocompatible carbon material has been obtained by the following sequence of steps:

- introducing a preformed substrate into an atmosphere of gaseous monomer vinylidene chloride (1,1 di-chloro ethylene);
- inducing a graft-polymerization reaction and grafting a uniform layer of polyvinylidene chloride on the substrate; and
- substantially eliminating and removing hydrogen chloride (dehydrochlorination reaction) from the polyvinylidene chloride layer in order to convert the polyvinylidene chloride layer into a coating of biocompatible carbon material.

Preferably, the dehydrochlorination reaction has been performed to such an extent that a residual chlorine content of the layer or coating amounts to less than 6% based on the chlorine content of the original polyvinylidene chloride layer.

Typically, a thus obtained coating comprising a thickness larger than 5 microns, is chemically bound to the substrate material and consists essentially of a pure carbon material comprising excellent biocompatible characteristics. The gas phase graft-polymerization reaction and the dehydrochlorination reaction may be effected under those conditions which do not affect substantially the mechanical properties of the substrate material. The coating is flexible and is bound inseparably to the substrate. Practically, the coating may comprise a coating thickness varying in a large range according to the specific demand.

A further important aspect of the present invention is related to a method of manufacturing said biocompatible material. The method according to the present invention comprises the following steps:

- providing a prepared substrate made of a polyolefin material;

introducing the substrate into a reactor vessel equipped for hermetic sealing;

providing an atmosphere of gaseous monomer vinylidene chloride (1,1 di-chloro ethylene) within the reactor vessel inducing within the reactor vessel a graft polymerization reaction and grafting a uniform polyvinylidene chloride layer on the substrate;

exposing the substrate which is partly or completely covered with a polyvinylidene chloride layer to conditions which cause the substantial elimination and removal of hydrogen chloride (dehydrochlorination reaction) from the polyvinylidene chloride layer in order to convert the polyvinylidene chloride layer into a coating comprising a biocompatible carbon material being chemically bound to the substrate.

According to a preferred embodiment of the present invention, the dehydrochlorination reaction will be at least continued until the residual chlorine content of the coating amounts to less than 6% based on the chlorine content of the original polyvinylidene chloride layer.

The biocompatible material according to the present invention may be especially obtained in the form of continuous fibers, filaments, threads or multifilament yarns made of polypropylene and comprising a chemically bound coating of biocompatible carbon material.

A further important aspect of the present invention relates to a specific use wherein the coated fibers, filaments, threads and multifilament yarns are used to prepare several kinds of medical prosthetic devices, for example such as artificial vascular grafts, artificial ligaments and tendons, suture rings for prosthetic heart valves, suture material and flexible fabrics and other coating materials for reconstructive surgery and other purposes, for example for closing burns, septum defects and the like.

BEST AND VARIOUS MODES FOR CARRYING OUT INVENTION

The substrate material as used within the scope of the present invention is a polyolefin material. Suitable polyolefin materials include especially polyethylene and polypropylene and other higher $\alpha$-olefins. Especially preferred are substrates made of a polypropylene material. The term "polypropylene material" shall include all kinds of polypropylene polymers which are used in the medical and biological field, including polypropylene copolymers with other $\alpha$-olefins, polypropylene homopolymers and mixtures of different polypropylene polymers. Further, modified polypropylene materials may be used comprising a molecular weight which has been reduced and selected in specific ranges in order to provide distinctive mechanical properties. As known in the art, a specific reduction of the molecular weight of polypropylene materials may be obtained by radical reaction with peroxide or similar reagents.

Other polymers which are commonly used in the medical field are less suited as substrate materials with the present invention. For example, polytetrafluororethylene (TEFLON) would be destroyed by the $\gamma$-radiation which is preferably used for inducing the radical graft polymerization reaction. Polyesters, such as DACRON, would be hydrolyzed by the conditions provided for the dehydrochlorination reaction of the polyvinylidene chloride.

The polyolefin material, especially polyethylene and polypropylene, is preferably shaped like fibers, filaments, threads, multifilament yarns, films and foils. Preferably, oriented starting materials will be used. The orientation of the carbon chain obtained by drawing the starting materials facilitates the deposition of a uniform coating of biocompatible carbon material. Preferably, the gas phase graft polymerization reaction may be effected under those reaction conditions which provide epitaxial growing of the polyvinylidene chloride layer on the substrate material. The grafted polyvinylidene chloride layer simulates or adopts the structure of the underneath substrate. A previous drawing operation generates an orientation of the substrate which provides a good starting structure of the following graft polymerization reaction. The starting material may comprise, for example, commercially available fiber-forming polypropylene or film-forming polyethylene. Preferably, polypropylene fibers have been drawn to a 6- or 7-times ratio of the original length. Preferably, polyethylene fibers or films have been drawn to a 4- or 5-times ratio of the original dimension.

The starting material for preparing the coating comprises vinylidene chloride (1,1 di-cloroethylene). Commercially available pure and stabilized preparations comprise a purity of more than 99.5%. Monomer liquid vinylidene chloride comprises a boiling point of about 30 to 32° C. Preferably, a de-gassing treatment of the monomer liquid vinylidene chloride at reduced pressure will be effected prior to the use thereof. The monomer vinylidene chloride starting material shall be free of air.

Preferably, the liquid monomer vinylidene chloride may be poured or sucked into an evaporator vessel which is arranged distantly to the reactor vessel and connected with the reactor vessel via a pipe or tube. The liquid monomer vinylidene chloride is evaporated within the evaporator vessel in order to generate gaseous monomer vinylidene chloride which is fed into the reactor vessel through the pipe or tube. The pipe or tube is equipped with valve means in order to control the amount and the vapor pressure of the gaseous vinylidene chloride fed into the reactor vessel. The evaporation rate may be controlled in order to maintain the vapor pressure of the vinylidene chloride within a certain range. Preferably, the vapor pressure of monomer vinylidene chloride within the reactor vessel is maintained below 1 bar.

The method according to the present invention provides for inducing a graft polymerization reaction within a gas phase of monomer vinylidene chloride in order to graft or deposit a uniform layer of polyvinylidene chloride on the substrate. The graft polymerization is based on a radical polymerization reaction. The present graft polymerization may be induced in several ways, for example by means of a laser light activation. Basically, the graft polymerization procedures as disclosed in the abovereferenced British Patents 856,329 and 801,531 may be used; however, the uniformity and regularity of the grafted polyvinylidene chloride layer and the yield to be obtained would be poor. According to a preferred aspect, the present invention looks for a radiation induced graft polymerization reaction by means of ionizing radiation which provides a chemical bonding of the coating via covalent C—C bonds to the substrate material in order to obtain a uniform and dense coating. Preferably, the radiation source comprises especially a gamma radiation source. Gamma rays comprise a high penetration power. The radiation may penetrate through the material of the reactor vessel, for example stainless steel. Several hermetically sealed reactor vessels may be arranged adjacent to a gamma radiation source in order to induce and perform the graft polymerization reaction within the vessels. Radiation by electron beams emanating from an electron accelerator device would be less suited because only relatively thin layers could be activated by electron radiation. A well suited and preferred gamma radiation source according to the present invention comprises the $_{60}^{27}$ Co isotope.

When grafting polyvinylidene chloride on oriented polypropylene fibers by means of the radiation included graft polymerization reaction according to the present invention, those conditions would be preferred which yield within the reactor vessel a dose rate of from 0.1 to 1.5 watt per kg radiated material; this corresponds to 10 to 150 rad/sec. Preferably the radiation may be continuously operated throughout the complete duration of the graft polymerization reaction.

By means of this radiation induced gas phase graft polymerization reaction, a uniform polyvinylidene chloride layer may be obtained and chemically bound to the polyolefin material of the substrate without impairing the mechanical characteristics of the substrate material. The polyvinylidene chloride is bound via covalent C—C bonds to the carbon chain of the substrate material. The layer thickness of the grafted polyvinylidene chloride layer may be varied in a wide range. For example, thin fibers having a diameter corresponding to several tex may be coated in this manner with a polyvinylidene chloride layer without any damage.

The fore-mentioned radiation induced graft polymerization reaction may be preferably effected within a still gas phase consisting of monomer vinylidene chloride. Furthermore, it is helpful to move the substrate with respect to the radiation source. In the case of coils consisting of wound-up foils or fibers, such coils may be rotated continuously around their axes. Furthermore, it is preferred to use relatively mild reaction conditions and an extended reaction duration instead of strong conditions within a short term. During the graft polymerization reaction the forming of a liquid vinylidene chloride phase oil the substrate and/or within the reactor vessel is to be avoided. Grafting from a liquid vinylidene chloride phase would yield non-uniform products. Preferably, the pressure of the gas phase consisting of monomer vinylidene chloride is maintained in the range of from about 500 to 700 mbar (milli bar). Under these conditions, the monomer vinylidene chloride will condense at a temperature of about 20° C. Preferably, the substrate material and the material of the wall of the reactor vessel will be maintained at a higher temperature. Especially preferred, the temperature of the substrate and of the reactor vessel wall will be maintained in the range of from about 25 to 50° C. The graft polymerization reaction is an exotherm reaction, and during an extended duration of reaction the substrate temperature may raise to about 40° C. In case of a substrate consisting of polypropylene fibers, the preferred fiber temperature shall not exceed about 30 to 40° C. The dose rate of the radiation may be controlled accordingly in order to avoid a substrate temperature higher than 40° C. Preferably the dose rate will be maintained within the range of from 0.1 to 1.5 watt per kg radiated material, as stated above. It is preferred to extend the duration of reaction instead of increasing the dose rate. Preferably, the radiation induced graft polymerization will be continuously performed for a duration of at least 20 hours; even a duration of 30 to 40 hours is not uncommon under practical conditions. Preferably, the radiation action will be continuously maintained during the complete duration of the gas phase graft polymerization reaction.

During this gas phase graft polymerization reaction, the gaseous monomer vinylidene chloride penetrates the substrate material, for example a polypropylene fiber and/or a coil made of wound-up polypropylene fibers. Typically, the diffusion rate of the gaseous monomer vinylidene chloride is higher than the rate of consumption of gaseous monomer vinylidene chloride caused by the graft polymerization reaction. This means the graft polymerization reaction proceeds from an equilibrated concentration of gaseous monomer vinylidene chloride. The formed polyvinylidene chloride will be chemically bound and anchored within the substrate material. Furthermore, the polyvinylidene chloride will grow uniformly on the substrate surface and will form a uniform and dense layer. It is preferred to maintain such reaction conditions which cause a structure of the polyvinylidene chloride layer which resembles the structure of the substrate material (epitaxial growing or deposition process). This kind of homology of structures is helpful to obtain an oriented layer of a distinctive carbon material providing biocompatibility. The growing or depositing of the polyvinylidene chloride layer is not limited by inherent factors and may be continued as desired. Finally, the duration of the graft polymerization reaction and thus the layer thickness of the grafted polyvinylidene chloride layer will be selected with respect to the intended use.

In general, all these reaction conditions will be optimized in order to obtain under mild conditions a uniform polyvinylidene chloride layer which is chemically bound to the substrate without impairing the substrate material. Even coils of polypropylene fibers or yarns may be treated under these conditions.

In case of relatively thin and extended substrates such as foils, films, fibers or yarns, preferably 0.1 to 1.2 parts per weight of polyvinylidene chloride may be deposited on 1 part per weight of substrate material under the conditions of a radiation included gas phase graft polymerization reaction. Even more preferred, 0.7 to 1.0 parts per weight of polyvinylidene chloride may be deposited on 1 part per weight of substrate material.

Using the fore-mentioned conditions, preferably 70 to 80 parts per weight of polyvinylidene chloride may be grafted on a fiber coil consisting of 100 parts per weight of polypropylene fibers, such that the coated fiber coil will comprise a complete weight of 170 to 180 parts per weight following the graft polymerization reaction. During the graft polymerization reaction, the thickness of the fibers or yarns will increase accordingly. Therefore, the density of the coils will increase, and it is preferred to provide a step of re-coiling prior to the following treatment. In case of a substrate comprising prior shaped formed bodies, a minor amount of deposited polyvinylidene chloride may be sufficient. It is necessary and sufficient to deposit only such an amount of polyvinylidene chloride which will form a uniform and continuous coating of a biocompatible carbon material during the dehydrochlorination step. Preferably, the coating of biocompatible carbon material may comprise a layer thickness of at least 5 micron.

Hydrogen chloride (HCI) has to be eliminated and removed substantially completely from the thus obtained polyvinylidene chloride layer in order to convert the polyvinylidene chloride layer into a coating consisting essentially of a pure carbon material having biocompatible characteristics. This reaction is termed dehydrochlorination reaction. Further, those conditions of the dehydrochlorination reaction have to be selected which cause a minimum of damage or impairment of the substrate material, and especially of the mechanical properties of the substrate material.

Efforts have been made to perform the dehydrochlorination reaction by means of metallic sodium and/or sodium amide within liquified ammonia. Basically, this type of reaction is possible on a laboratory scale, but requires a very extended duration of reaction of 100 hours and more and further requires working under high pressure (50 bar and more) within an autoclave. The productivity of this type of reaction is too poor for working on an industrial scale. Further, non-reacted sodium amide has to be decomposed and removed, for example by means of a substantial amount of methanol.

Further efforts have been made to perform the dehydrochlorination reaction by means of gaseous ammonia in a gas phase reaction. Basically, this kind of reaction is possible, but in practical operation only very small samples have been successfully treated. A sufficient rate of reaction requires temperatures above 100° C. On the other hand, the substrate temperature, especially in the case of polypropylene fibers or yarns, shall not exceed temperatures of 100 to 120° C. The dehydrochlorination reaction is an exotherm reaction. When working in a gas phase environment, there is only a limited possibility of heat elimination, and therefore, overheating of the fibers may occur easily. Further, when working in an ammonia gas phase, the ammonium chloride ($NH_4Cl$) formed by the dehydrochlorination reaction within an ammonia atmosphere cannot be removed easily.

It is an essential object of the present invention to provide conditions of a dehydrochlorination reaction which are suited for working on an industrial scale, which do not impair the mechanical properties of the substrate material, and which eliminate and remove hydrogen chloride (HCl) to a substantial amount from the polyvinylidene chloride in order to convert the polyvinylidene chloride layer of a coating of a biocompatible carbon material. Preferably, the dehydrochlorination reaction shall reduce the residual chlorine content of the carbon coating to less than 6%, based on the chlorine content of the original polyvinylidene chloride layer. Even more preferred is a residual chlorine content in the carbon coating of less than 3%, based on the chlorine content of the original polyvinylidene chloride layer.

According to a preferred and essential aspect of the present invention, this dehydrochlorination reaction will be performed by means of a hot aqueous alkaline solution. Preferably, the substrate comprising the grafted polyvinylidene chloride layer will be dipped into a hot aqueous alkaline solution and will be maintained within the solution for at least several hours. Alternatively, the hot aqueous alkaline solution may be pumped through a reactor chamber wherein the substrate comprising the grafted polyvinylidene chloride layer is arranged within the reactor chamber. In case of coils consisting of polypropylene fibers or yarns and being coated with a grafted polyvinylidene chloride layer, the hot aqueous alkaline solution may be pumped through the coils which are arranged within a reactor vessel.

Preferred is a treatment at or below the boiling temperature of the aqueous solution. A temperature of the aqueous solution of about 80 to 100° C. has proved quite effective and may be preferred.

By working at a temperature at or below 100° C., impairment of the substrate material may be avoided. The boiling point of the solution avoids a higher substrate temperature. Further, an aqueous solution comprises a high thermal capacity. When working within an aqueous solution, a higher rate of reaction may be obtained and controlled, because the heat developed by the exothermic dehydrochlorination reaction may be eliminated easily. The chloride salt formed by the dehydrochlorination reaction dissolves easily within an aqueous solution and may be removed easily.

In order to provide an aqueous alkaline solution, typical alkaline reagents such as inorganic bases and salts may be used, for example sodium hydroxide or potassium hydroxide or the carbonates and bicarbonates of alkali metals and alkaline earth metals. Organic bases such as amines did not provide satisfying results. When working in an aqueous NaOH or KOH solution, it might be helpful to add a phase transfer catalyst such as for example tetrabutylammonium-bromide (($CH_3CH_2CH_2CH_2$)$_4$NBr).

A mostly preferred dehydrochlorination agent is hot concentrated aqueous ammonia. An ammonia concentration of 20 to 35% by weight has provided good results. Preferably, commercially available concentrated aqueous ammonia (ammonia hydroxide) may be used comprising an ammonia concentration of about 25% by weight. According to a further preferred aspect, an aqueous ammonia solution will be used which is saturated at the given temperature, and a necessary excess pressure of gaseous ammonia will be provided. For example, an excess pressure of ammonia of from about 6 to 8 bar may be provided. For example, especially good results have been obtained under the following conditions:

a hot aqueous ammonia comprising an ammonia concentration of about 25% by weight;

an operation temperature of about 96° C. and an excess pressure of ammonia of about 6 bar.

Under these relatively mild dehydrochlorination conditions, the dehydrochlorination reaction by means of hot concentrated aqueous ammonia will be maintained for a duration which is sufficient for substantial elimination and removal of hydrogen chloride from the polyvinylidene chloride and to convert the polyvinylidene chloride into a coating of a biocompatible carbon material. Typically, a duration of at least 20 hours may be required. According to a preferred embodiment of the present invention, this type of dehydrochlorination reaction by means of hot concentrated aqueous ammonia shall reduce the residual chlorine content of the carbon coating to less than 6% based on the chlorine content of the original polyvinylidene chloride layer. In this case, the dehydrochlorination reaction may be performed for a duration of about 30 to 40 hours and more.

Even more preferred, the dehydrochlorination reaction may be performed for a sufficient duration in order to reduce the residual chlorine content of the coating to less than 3% based on the chlorine content of the original polyvinylidene chloride layer. The chlorine forming the residual chlorine content of the coating is termed "the structurally bound chlorine", i.e. the chlorine contained in residual amounts of polyvinylidene chloride within the carbon coating. This structurally bound chlorine may be detected by means of infrared spectroscopy at absorption bands at about 1050 $cm^{-1}$. A residual content of structurally bound chlorine of less than 3% will provide a coating consisting essentially of a pure carbon material comprising outstanding biocompatible characteristics.

Following the dehydrochlorination reaction, a carbon material will be obtained comprising a density of about 1.8 g/cm$^3$. Spectroscopic measurements by means of infrared spectroscopy confirm absorption bands at 2180 $cm^{-1}$ and wide absorption bands at about 1600 $cm^{-1}$. The absorption bands at 2180 $cm^{-1}$ will be adopted to the stretching vibrations of C≡C triple-bonds in linearly conjugated carbine structures. The absorption bands at 1600 $cm^{-1}$ will be adopted to conjugated C═C double-bonds. According to these experimental results the inventors assume—without any acceptance to be bound to this theory—that the substantially exhaustive dehydrochlorination reaction of the grafted polyvinylidene chloride layer will provide a carbon material comprising an oriented carbine structure.

Typically, the content of the thus formed carbon material may range from about 10 to 20% per weight based on the complete weight of a coated polypropylene fiber or yarn; this means that the final fiber or yarn, comprising a coating of biocompatible carbon material, consists of 80 to 90% per weight of polypropylene material and consists of 20 to 10% per weight of the carbon material, each based on the complete weight of the coated fiber or yarn.

Following the dehydrochlorination reaction, the coated substrate will be subjected to an extended washing or rinsing treatment, preferably by means of hot water in order to especially remove ammonium chloride. The content of ammonium chloride may be detected by means of infrared spectroscopy at absorption bands at about 1400 $cm^{-1}$. Preferably, the residual content of ammonium chloride shall be reduced to less than 0.1% per weight based on the complete weight of the coated substrate material. In order to achieve this goal, a several hours washing treatment using hot water comprising a temperature of about 80 to 90° C. is well suited.

Following the washing or rinsing treatment, a heat treatment may be provided. Especially in the case of substrates comprising fibers, filaments, threads, multifilament yarns, foils and films, the heat treatment provides a thermosetting of the elongated structures, especially of the fiber structure. Preferably, the heat treatment may be performed within a vacuum drier cabinet comprising a reduced pressure of less than 0.1 mbar, whereby a pumping operation will be maintained continuously. In the case of coils made of wound-up coated fibers, a thermosetting may be achieved at a temperature of 135° C. for a duration of about 1.5 hours within vacuum space. In addition, this type of heat treatment will remove residual traces of ammonium chloride by sublimation.

Substrates of any shape may be subjected to the forementioned radiation induced gas phase graft polymerization reaction and the following dehydrochlorination reaction by means of hot concentrated aqueous ammonia. For example, the substrates may comprise pre-shaped formed bodies, such as injection molded parts. For example, these types of pre-formed shaped bodies may comprise housing parts and components of oxygenators, dialyzer apparatus, filtration devices and heat exchangers, further infusion instruments, connectors, tubes and hoses and similar other devices and instruments. Further, the pre-formed substrate may comprise fabrics made of polypropylene fibers or yarns suited as coating materials, for example for coating and covering of septum defects. Further, the pre-formed substrate may comprise tubes and hoses for the manufacture of vascular prosthetic devices (grafts). Further, the pre-formed substrate may comprise suture rings of artificial prosthetic heart valves. Further, the pre-formed substrate may comprise other materials, devices and components intended for prolonged or permanent implantation in a living body and/or intended for contact with blood or plasma within equipment for maintaining extracorporal circulation of blood and/or plasma. A biocompatible carbon material according to the present invention may be deposited on the above stated pre-formed substrates. However, it has to be recognized that the additionally deposited coating of carbon material may in some cases provide a cross-linking and stiffening of the substrates.

According to an alternative and more preferred embodiment of the present invention, the substrate comprises continuous fibers, filaments, threads, multifilament yarns, hollow fibers, films or foils which are commonly termed "continuous materials". These continuous materials are wound on a perforated coil carrier such as a sleeve, a bobbin or a cartridge in order to obtain coils. The coils are introduced into the reactor vessel and the gas phase graft polymerization reaction will be effected with those coils. Thereafter, the treated coils will be introduced in another reactor vessel for effecting the dehydrochlorination reaction, and the dehydrochlorination reaction will be effected by means of a hot concentrated aqueous ammonia solution. The reaction proceeds through the coil and effects the complete wound-up material. Here, it is recommended to maintain the thickness of the wound-up continuous material on the perforated coil carrier less than about 20 mm and/or to maintain the density of the wound-up material in a range of from about 0.40 to about 0.60 $g/cm^3$. Maintaining these conditions will provide good penetration of the complete continuous material by gaseous monomer vinylidene chloride or by aqueous ammonia. Several coils of this type may be introduced concurrently into a reactor vessel for the radiation induced gas phase graft polymerization reaction and may be treated concurrently. When performing the dehydrochlorination reaction, preferably each single coil will be introduced in its own apartment or chamber within the reactor vessel in order to obtain good penetration of the wound-up fiber mass by means of a forced flow of aqueous ammonia. However, several reactor vessels may be arranged parallel and combined into a group of vessels; the hot alkaline dehydrochlorination agent, especially hot concentrated aqueous ammonia, may be pumped serially through each vessel of the group of vessels. Despite the relatively extended duration of treatment, high productivity may be obtained when using such a group of vessels for performing the dehydrochlorination reaction.

During the gas phase graft polymerization reaction, a significant amount of polyvinylidene chloride will be deposited on the coiled continuous material wound-up on a coil carriers such that the density of the coil will increase. Following the gas phase graft polymerization reaction, it is recommended to recoil the coated continuous material and to wind-up the coated continuous material onto a new coil carrier under controlled conditions in order to obtain a coil density which is well suited for the following dehydrochlorination reaction in a liquid phase. The hot aqueous solution may be pumped continuously through the perforated coil carrier and the coiled fiber mass wound-up on the coil carrier.

The following example serves for a further explanation of the invention and may by no means be construed as a limitation of the invention.

EXAMPLE

The starting material is a multi-filament yarn comprising 36 oriented filaments each made of polypropylene. The multi-filament yarn comprises a length-related mass of 8 tex. For performing the steps of the method according to the present invention, the starting yarn will be re-coiled on a cylindric perforated cartridge consisting of a non-corrosive steel material and comprising a length of 185 mm and an external diameter of 30 mm. The re-coiling will be performed under conditions such as to obtain a wound-up yarn coil comprising a coil thickness of about 14 mm and comprising a coil density of about 0.50 to 0.55 $g/cm^3$. Accordingly, each coil will comprise about 170 to 180 g wound-up yarn.

The radiation induced gas phase graft polymerization reaction will be effected by introducing the coils into a gaseous phase of monomer vinylidene chloride and by additionally providing a radiation action. Accordingly, the coils will be introduced into a hermetically sealable reactor vessel equipped for evacuation. Preferably, the coils may be arranged within the reactor vessel for rotation about the coil axis. A container comprising an evaporator is arranged distantly to the reactor vessel and is connected with the reactor vessel via a pipe or tube being equipped with a shut-off valve. The container is additionally connected to a vacuum pump for evaporation and for a de-gassing treatment. The liquid monomer vinylidene chloride will be poured into the container and will be evaporated by means of the evaporator arranged within the container.

Having inserted several coils into the reactor vessel, the reactor will be closed and will be evacuated to a residual pressure of about 10 mbar. The liquid, monomer vinylidene chloride, which has been previously de-gassed under vacuum, will be introduced into the container. The introduced amount of vinylidene chloride is related to the complete amount of yarn to be coated and to the desired coating thickness. Following the introduction of vinylidene chloride into the container, the vinylidene chloride within the container will be de-gassed again. As far as necessary, the evaporator will be set into operation in order to generate gaseous monomer vinylidene chloride within the container. Thereafter the check valve will be opened in order to form a gas phase of monomer vinylidene chloride within the reactor vessel at ambient temperature. The temperature of the reactor vessel will be maintained at about 20 to 30° C. The vapor pressure of monomer vinylidene chloride will be controlled between about 500 and 700 mbar (millibar). Care shall be taken in order to avoid any condensation of liquid vinylidene chloride on the substrate and/or on the walls of the reactor.

The radiation action will be performed by means of one or more radiation source(s) comprising the reactive $^{60}$Co isotope. Thereto, the reactor vessel will be arranged within a safe-guarded room equipped such that the radiation source(s) may be introduced into said room from a shielded position. For example, regularly the radiation source(s) may be positioned within a deep hole in the ground beneath the floor of the room. In order to provide the radiation action, the radiation source(s) will be raised from the hole into the room and will be arranged adjacent to the reactor vessel such that the gamma radiation flux may penetrate the reactor vessel. The radiation source(s) and other conditions will be controlled such as to obtain within the reactor vessel a radiation dose rate of about 0.15 watt per kg radiated material; this corresponds to a radiation dose rate of about 15 rad/sec. The container containing the liquid vinylidene chloride is arranged distantly to the radiation source(s) and to the reactor vessel, and may be shielded with respect to the gamma radiation by means of lead bricks. The exposure of the reactor vessel to the radiation action will be continuously maintained during the complete graft polymerization reaction. The coils within the reactor vessel may be rotated, and the speed of rotation may be adjusted to and controlled along with the radiation dose rate.

When starting the radiation induced graft polymerization reaction, the liquid polyvinylidene chloride within the container may comprise a temperature of about 17 to 20° C. The radiation induced graft polymerization reaction is an exothermic reaction, and the heat developed during the reaction will increase the temperature of the yarn coil to about 35 to 40° C. The yarn temperature shall not exceed a temperature of about 40° C. A duration of reaction of about 30 to 35 hours is required, in order to deposit about 65 to 80 parts per weight polyvinylidene chloride on 100 parts per weight polypropylene yarn under these conditions. The reaction is terminated by a decrease of pressure within the system, which is caused by consumption of the monomer vinylidene chloride. Following termination of the reaction, the radiation source(s) will be moved toward its/their originally shielded and protected position. The volatile matters including residual vapors of vinylidene chloride within the reactor vessel will be pumped out and condensated within a cooling trap cooled by means of liquid nitrogen. Thereafter, fresh air is blow through the reactor vessel. The coils comprising the coated yarn will be removed from the reactor vessel. The coated yarn has a white lustrous appearance.

Following the radiation induced graft polymerization reaction, the coated yarn is recoiled onto another perforated coil carrier in order to obtain again coils comprising a density which is suited for the following dehydrochlorination reaction.

The dehydrochlorination reaction will be effected by pumping hot aqueous ammonia solution comprising 25% per weight ammonia through the perforated coil carrier and through the fiber coil wound-up on the carrier. The process is controlled by means of the differences in temperature and/or pressure within a feeding container and a receiving container for the aqueous ammonia solution. Each coil will be placed within a single apartment or chamber of a reactor vessel or within a single reactor vessel. The complete installation comprises a number of apartments, chambers or reactor vessels being connected in a serial arrangement. Before starting the dehydrochlorination reaction, the complete installation will be evacuated to a residual pressure of about 0.1 mbar. In the following, the aqueous ammonia will be pumped into the feeding container and will be heated to the prescribed temperature. This hot aqueous ammonia will be pumped out of the feeding vessel through the perforated coil carrier and through the fiber coil wound-up on the carrier into a receiving container and then out of the receiving container through the coil carrier and the fiber coil into the feeding container. Essentially, the aqueous ammonia comprises a temperature of 96° C., an ammonia concentration of 25% per weight, and within the closed installation there is an ammonia pressure of about 6 bar above the liquid aqueous ammonia solution. Maintaining these conditions, the dehydrochlorination reaction will be performed for a duration of about 35 hours.

Next, the treated fibers will be rinsed with hot water in order to remove ammonium chloride which has been formed as a by-product. For performing the rinsing or washing treatment, hot desalted water comprising a temperature of 80 to 95° C. will be pumped through the fiber coil for 5 hours.

Next, a thermosetting of the dehydrochlorinated and rinsed yarns will be performed in order to avoid thermal shrinkage during a subsequent use of the yarns (for example at a sterilization treatment using elevated temperatures) and in order to completely remove residual traces of ammonium chloride by sublimation. For the thermosetting treatment, the fiber coils will be maintained for at least 1.5 hours within a vacuum drier cabinet under the vacuum less than 0.1 mbar at a temperature of about 135° C.

Following the thermosetting treatment, yarn samples may be analyzed in order to verify the residual amount of structural chlorine and of ammonium chloride. "Structurally bound chlorine" means chemically bound chlorine contained within residual amounts of polyvinylidene chloride. This chemically bound chlorine may be detected by means of infrared spectroscopy at absorption bands at about 1050 cm$^{-1}$. Maintaining the above-mentioned conditions of a dehydrochlorination treatment, yarn coils may be obtained which contain less than 3% structurally bound chlorine based on the residual chlorine content of the original polyvinylidene chloride layer. Further, these yarn coils comprise less than 0.1% ammonium chloride based on the weight of the coated fiber or yarn. The coated yarn has a dull, deep black appearance and consists of 87% per weight of polypropylene and of 13% per weight of a biocompatible carbon coating, based on the weight of the coated yarn.

Next, the coated fibers or yarns may be re-coiled onto standard bobbins or cartridges which may be used for shipment to a finishing plant, for example to a manufacturer of artificial fabric vascular grafts. Preferably, a crosswise coiling scheme may be used for the re-coiling. The fiber mass per bobbin or cartridge shall not exceed an amount of about 250 g.

Fibers, threads, yarns and foils made of polyethylene, and hollow fibers, especially porous hollow fibers made of polypropylene, may be treated and coated in a similar process as described with the above-mentioned example.

The coated polypropylene yarns as obtained according to the fore-mentioned example and comprising a coating of a biocompatible carbon material may be used for manufacturing a number of different medical prosthetic devices suitable for prolonged or permanent implantation in a living body; for example these medical prosthetic devices include vascular grafts including coronary grafts, artificial ligaments and tendons, suture material, suture rings for artificial prosthetic heart valves, woven and non-woven fabrics and other covering materials and other pieces in the field of medical prosthetic devices.

Coated yarns as obtained by the fore-mentioned examples have been used to prepare knitted hoses by means of a circular or crosswise knitting machine. The hoses are intended for implantation as vascular grafts comprising an inner diameter of 5 to 12 mm and a length up to 600 mm. A part of the hoses comprises a smooth even wall face. Another part of the hoses comprises a corrugated structure (so-called accordion-like structure). The hoses have a deep black appearance. The coating made of biocompatible carbon material is bound firmly and inseparably to the substrate and may not be scratched off from the substrate. These hoses have been implanted as vascular grafts, for example in the positions aorto-bifemoral, aorto-iliofemoral, hip-thigh-hollow of the knee, axillaris-thigh-hollow of the knee thigh or leg (venous)

thigh-tibia.

The main blood circulation within the damaged areas could be rehabilitated with great reliability by means of the artificial vascular grafts. The vascular grafts provided good thromboresistance and showed good resistance with respect to infectious inflammation (as far as in the distal areas of the extremities findings in the form of matter or abscessies have been established from the beginning).

Further vascular grafts of this type comprising a diameter of from 5 to 10 mm have been used in surgery operations of by-passes at the lower extremities and at peritoneal vasoramifications of the aorta. During the operations and during the following 6-month-term of observation, not a single case of intraoperative thrombosis or of impermeability of the artificial graft has been found.

Further, the coated yarn as obtained by the fore-mentioned example has been used to prepare braided or twisted bands or ribbons which may be used as artificial ligaments and tendons. The bands or ribbons have been implanted in order to treat instabilities of the knee-joint or of the crucial ligament of the knee, or for the treatment of a plasticity of the Achilles tendon or for the forming of a crosswise plantar bow of the sole of the foot. These experiments provided good results. Results of histological and histochemical examination of the tissue reactions caused by inner joint implants and outer joint implants made of this new material have confirmed the biological compatibility of this new material. Further, these experiments and results have confirmed the spreading and penetration of connecting tissue into the outer layers of the implants. In no case has a decomposition or degradation of the new material according to the present invention been determined. These implants exhibit extraordinarily good tissue compatibility and stimulate growth of the oriented collagen tissue. Stabilization of the tendon system within the knee-joint (crucial ligament) and a complete reproduction of its function was obtained with all patients.

A further aspect of the present invention concerns the use of the biocompatible material according to the present invention.

Preferably, the biocompatible material according to the present invention may be used in places and circumstances where compatibility with blood, plasma and/or tissue is important. This kind of biocompatibility is especially important in relation to prosthetic devices, implants, and surfaces of extracorporal blood circulation devices which may be contacted by blood or plasma.

A preferred aspect of the present invention concerns the use of the new biocompatible material according to the present invention having the form of continuous fibers, threads or multi-fiber yarns made of polypropylene material and comprising a coating of biocompatible carbon material for the preparation of artificial grafts, vascular grafts, coronary grafts and the like. For example, vascular grafts may be obtained from fabrics made of those fibers or yarns or may be obtained by knitting or braiding those fibers, threads or yarns in order to obtain hoses. For example, seamless hoses of the kind comprising an inner diameter of about 3 to 5 mm may be used in order to replace defective coronary vessels. Hoses of this type and comprising a diameter of about 5 to 60 mm may be used in order to replace defective veins or arteries. Optionally, hoses comprising a larger diameter may additionally be provided with a corrugated structure (accordion-like structure) in order to increase the flexibility of those artificial vascular grafts.

Another preferred aspect of the present invention concerns the use of the biocompatible material according to the present invention having the form of continuous fibers, threads or yarns made of polypropylene material and comprising a coating with biocompatible carbon material for the preparation of suture rings for artificial prosthetic heart valves. Typically, the artificial prosthetic heart valves comprise one or two occluders pivoting around an axis being fastened to a ring. The ring may be made of pyrolytic carbon, titanium or of another suited material and comprising a circumferential groove at the outer circumference. A suture ring made of textile material is constrained within the grooves and serves to fasten the artificial prosthetic heart value to the natural tissue. Preferably, this type of suture ring may be made of the biocompatible material according to the present invention.

Another preferred aspect of the present invention concerns the use of the biocompatible material according to the present invention having the form of continuous fibers, threads or yarns made of polypropylene material and comprising a coating with a biocompatible carbon material as suture material for surgery purposes and/or for the preparation of suture material for surgery purposes. Depending upon the specific circumstance and field of use, the suture material may comprise a thickness of from 0.1 to 10 mm. Suture yarn according to the present invention exhibits high tear strength, high resistance against enzymatic degradation and good tissue compatibility. Knots may be formed in the suture yarn without any delamination of the carbon coating. All of these features characterize good suture material for surgery purposes.

Another preferred aspect of the present invention concerns the use of a biocompatible material according to the present invention having the form of continuous fibers, threads or yarns made of polypropylene and comprising a coating with a biocompatible carbon material for the preparation of artificial ligaments and tendons. Typically, the ligaments and tendons comprise bands or ribbons or thicker yarns knitted or braided of fibers or threads according to the present invention. For example, these bands or ribbons may be used with success for the stabilization of the tendon system of the knee-joint as explained in more detail above.

A further preferred aspect of the present invention concerns the use of a biocompatible material according to the present invention having the form of continuous fibers, threads or yarns made of polypropylene material and comprising a coating with a biocompatible carbon material for the preparation of woven and non-woven fabrics or cushions. For example, those fabrics or cushions may be used as covering material, for example for the care of burns and sores, in general for covering wounds and closing holes, openings, fractures, ruptures and the like, for closing inner wall defects of the heart, for extension of the working sections of the main arteria of the lungs, as closing material for closing septum defects, and the like.

A further aspect of the present invention concerns the use of the biocompatible material according to the present invention having the form of plates or patches, which are conventionally used for fastening surgical seams and sutures. For example, those patches may comprise dimensions of from 5×2 mm to 12×5 mm.

Another preferred aspect of the present invention concerns the use of the biocompatible material according to the present invention having the form of extendable thin-walled tubes or hoses, optionally of corrugated structure for lining the inner surface of femoral stents. "Stents" means prosthetic devices for long-term expanding and maintaining open of natural vessels and grafts. Typically, a stent comprises a tubular-like diamond-shaped construction made of a thin filament of a memory metal allow (for example such as "NITINOL"). The stent is prepared in the form of a thin flexible tube which may be introduced into the defective vessel by means of an application device. The body temperature and the natural humidity cause the tubular-like diamond-shaped structure made of a specific memory metal alloy to expand several times the original diameter and cause long-term maintenance of the self-expanded structure within the living body. Therefore, these femoral stents may be used for long term expansion of natural vessels. According to a specific aspect of the present invention, a thin-walled tube made of a coated polypropylene material according to the present invention is provided within the tubular-like diamond-shaped metal construction. This thin-walled tube will expand along with the diamond-shaped metal construction. The expanded tube avoids direct contact of blood with the metal construction of the stent and avoids or inhibits any clotting or thrombus forming at the diamond-shaped metal construction.

Finally, shaped bodies, such as injection molded parts made of polyethylene material or polypropylene material may be obtained according to the present invention. The bodies or parts or components comprise a coating of biocompatible carbon material on at least a part of their surface or on their complete surface. For example, those shaped bodies or parts may comprise components or housing parts of oxygenators, dialyzer apparatus, blood filter apparatus. heat exchangers, cardiotomy-reservoir vessels, blood infusion instruments, haemoconcentrator devices, heart-lung machines and/or other devices of extra-coiporal blood circulation. Further, those shaped bodies, parts or pieces may comprise connectors having different diameters and dimensions, tubes and hoses including tubes and hoses for perfusion purposes.

Skilled persons in the art may consider many other fields of application of the biocompatible materials according to the present invention, especially applications in areas where good compatibility of the substrate with blood, plasma and/or tissue is important.

We claim:

1. A biocompatible material comprising a substrate made of a polyolefin material, and having a coating of biocompatible carbon material chemically bound to said substrate wherein said coating is obtained by a process comprising the following steps:

introducing a preformed substrate into an atmosphere of gaseous monomer vinylidene chloride;

inducing a graft-polymerization reaction and grafting a uniform layer of polyvinylidene chloride on said substrate; and substantially eliminating and removing hydrogen chloride from said polyvinylidene chloride in order to convert said polyvinylidene chloride layer into a chemically bound coating of biocompatible carbon material.

2. A biocompatible material according to claim 1 wherein said coating of biocompatible carbon material has a residual chlorine content of less than 6% based on the chlorine content of the original layer of polyvinylidene chloride.

3. A biocompatible material according to claim 1, wherein said graft polymerization reaction is a gas phase graft polymerization induced by ionizing radiation.

4. A biocompatible material according to claim 3, wherein said graft polymerization reaction is induced by ionizing radiation having an average dose rate of from about 0.1 to about 1.5 watt per kg radiated material.

5. A biocompatible material according to claim 4, wherein said graft polymerization reaction continues for a duration of at least 20 hours.

6. A biocompatible material according to claim 3, wherein said ionizing radiation is gamma radiation.

7. A biocompatible material according to claim 1, wherein 0.1 to 1.2 parts per weight of polyvinvlidene chloride have been grafted on 1 part per weight of said substrate.

8. A biocompatible material according to claim 1, wherein 0.7 to 1.0 parts per weight of polyvinlidene chloride have been grafted on 1 part per weight of said substrate and wherein said substrate is a fiber.

9. A biocompatible material according to claim 1, wherein said dehydrochlorination reaction comprises treatment with a hot concentrated aqueous ammonia solution.

10. A biocompatible material according to claim 9, wherein said dehydrochlorination reaction continues for a duration of at least 20 hours.

11. A biocompatible material according to claim 1, wherein said dehydrochlorination reaction provides a residual chlorine content of less than 3%, based on the chlorine content of the original layer of polyvinylidene chloride.

12. A biocompatible material according to claim 1, wherein the coating has a thickness of more than 5 microns.

13. A biocompatible material according to claim 1, wherein the substrate is a member selected from the group consisting of a fiber, a filament, a thread and a yarn and said polyolefin is a polypropylene material.

14. A biocompatible material according to claim 13, wherein the polypropylene material has been oriented by a drawing step.

15. A biocompatible material according to claim 13, wherein the substrate comprises an oriented fiber or a multifilament yarn of oriented filaments, each consisting of a polypropylene material;

wherein the coating comprises a carbon material having a density of approximately 1.8 g/cm$^3$; and wherein the amount of said carbon material is about 10 to 20% per weight based on the total weight of the coating and fiber or yarn.

16. A biocompatible material according to claim 13, wherein the amount of said carbon material is about 10 to 20% per weight based on the total weight of the coating and fiber or yarn.

17. A biocompatible material according to claim 1, wherein said biocompatible carbon material is flexible and bound inseparably to said substrate.

18. A biocompatible material according to claim 1, wherein said coating of biocompatible carbon material is covalently bonded to said substrate by C—C bonds to the carbon chain of the substrate.

19. A biocompatible material according to claim 1, wherein said layer of polyvinylidene chloride is an epitaxial layer.

20. A biocompatible material according to claim 19, wherein said coating consists essentially of pure carbon with a residual chlorine content of less than 3% based on the chlorine content of the original layer of polyvinylidene chloride.

21. The biocompatible material of claim 1, wherein said dehydrochlorination reaction comprises treating with a hot aqueous ammonia solution comprising an ammonia concentration of 20 to 35% by weight.

22. The biocompatible material of claim 1, wherein said dehydrochlorination reaction is carried out at a temperature from 80° C. to 100° C.

23. The biocompatible material of claim 1, which further comprises after said dehydrochlorination reaction, rinsing said substrate with hot water.

24. The biocompatible material of claim 23, which further comprises after said rinsing, heating said substrate under reduced pressure.

25. The biocompatible material of claim 1 wherein said polyolefin is a copolymer of propylene with another α-olefin.

* * * * *